(12) United States Patent
Schlick et al.

(10) Patent No.: US 10,716,659 B2
(45) Date of Patent: *Jul. 21, 2020

(54) STENT

(71) Applicant: BOSTON SCIENTIFIC SCIMED, INC., Maple Grove, MN (US)

(72) Inventors: Tilman Schlick, Esslingen (DE); Markus Kuhnle, Urbach (DE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 265 days.

This patent is subject to a terminal disclaimer.

(21) Appl. No.: 15/846,906

(22) Filed: Dec. 19, 2017

(65) Prior Publication Data

US 2018/0104043 A1 Apr. 19, 2018

Related U.S. Application Data

(63) Continuation of application No. 15/401,197, filed on Jan. 9, 2017, now Pat. No. 9,872,758, which is a
(Continued)

(51) Int. Cl.
| | |
|---|---|
| *A61F 2/04* | (2013.01) |
| *A61F 2/89* | (2013.01) |
| *A61F 2/90* | (2013.01) |
| *A61F 2/07* | (2013.01) |
| *A61F 2/88* | (2006.01) |

(Continued)

(52) U.S. Cl.
CPC .................. *A61F 2/04* (2013.01); *A61F 2/07* (2013.01); *A61F 2/82* (2013.01); *A61F 2/88* (2013.01); *A61F 2/89* (2013.01); *A61F 2/90* (2013.01); *A61F 2/2418* (2013.01); *A61F 2002/044* (2013.01); *A61F 2002/075* (2013.01); *A61F 2002/30233* (2013.01); *A61F 2002/30235* (2013.01); *A61F 2002/30327* (2013.01); *A61F 2002/828* (2013.01); *A61F 2230/0069* (2013.01); *A61F 2230/0078* (2013.01);
(Continued)

(58) Field of Classification Search
CPC ...... A61F 2/04; A61F 2/89; A61F 2/90; A61F 2/88; A61F 2002/044; A61F 2230/0069; A61F 2002/828; A61F 2250/0007; A61F 2250/001; A61F 2230/0078; A61F 2250/0039
USPC ....... 606/191, 194, 195, 198; 623/1.11, 1.15
See application file for complete search history.

(56) References Cited

U.S. PATENT DOCUMENTS

| | | |
|---|---|---|
| 4,655,771 A | 4/1987 | Wallsten |
| 5,380,270 A | 1/1995 | Ahmadzadeh |
| (Continued) | | |

FOREIGN PATENT DOCUMENTS

| | | |
|---|---|---|
| DE | 9390115 U1 | 12/1994 |
| DE | 69526857 T2 | 1/2003 |
| (Continued) | | |

*Primary Examiner* — Vy Q Bui
(74) *Attorney, Agent, or Firm* — Seager, Tufte & Wickhem, LLP

(57) ABSTRACT

A stent for transluminal implantation comprises a first, second and third stent section for splinting and/or keeping open a hollow organ which are connected to each other via elastic tubular sections. The stent combines at least three different stent designs in one stent and can therefore be adjusted to the motion behavior of a hollow organ in an improved fashion.

20 Claims, 2 Drawing Sheets

Related U.S. Application Data continuation of application No. 13/763,169, filed on Feb. 8, 2013, now Pat. No. 9,554,924, which is a continuation of application No. 12/768,447, filed on Apr. 27, 2010, now Pat. No. 8,372,134, which is a continuation of application No. 11/059,840, filed on Feb. 17, 2005, now Pat. No. 7,731,742, which is a continuation of application No. 10/427,869, filed on Apr. 30, 2003, now abandoned.

(51) Int. Cl.
*A61F 2/82* (2013.01)
*A61F 2/24* (2006.01)
*A61F 2/30* (2006.01)

(52) U.S. Cl.
CPC . *A61F 2250/001* (2013.01); *A61F 2250/0007* (2013.01); *A61F 2250/0039* (2013.01)

(56) References Cited

U.S. PATENT DOCUMENTS

| | | | |
|---|---|---|---|
| 5,873,906 A | 2/1999 | Lau et al. | |
| 5,888,201 A | 3/1999 | Stinson et al. | |
| 5,897,589 A | 4/1999 | Cottenceau et al. | |
| 6,001,123 A | 12/1999 | Lau | |
| 6,027,525 A | 2/2000 | Suh et al. | |
| 6,129,756 A | 10/2000 | Kugler et al. | |
| 6,156,064 A | 12/2000 | Chouinard | |
| 6,162,244 A * | 12/2000 | Braun | A61F 2/82 623/1.12 |
| 6,517,570 B1 | 2/2003 | Lau et al. | |
| 6,669,724 B2 * | 12/2003 | Park | A61F 2/2418 623/1.24 |
| 6,767,358 B2 | 7/2004 | Leonhardt et al. | |
| 6,852,116 B2 | 2/2005 | Leonhardt et al. | |
| 6,929,659 B2 * | 8/2005 | Pinchuk | A61F 2/07 623/1.13 |
| 2006/0259123 A1 * | 11/2006 | Dorn | A61F 2/91 623/1.12 |
| 2008/0046065 A1 * | 2/2008 | Hartley | A61F 2/07 623/1.13 |

FOREIGN PATENT DOCUMENTS

| | | |
|---|---|---|
| DE | 10221076 A1 | 11/2003 |
| EP | 0775471 A1 | 5/1997 |
| EP | 0808614 A2 | 11/1997 |
| EP | 0818184 A1 | 1/1998 |
| EP | 0888758 A2 | 1/1999 |
| EP | 0901353 A1 | 3/1999 |
| EP | 0901353 B1 | 7/2001 |
| EP | 0775471 B1 | 5/2002 |
| EP | 1264582 A2 | 12/2002 |
| JP | 10043315 A | 2/1998 |
| JP | 10277068 A | 10/1998 |
| JP | 2001502192 A | 2/2001 |
| SU | 1292761 A1 | 2/1987 |
| WO | 0007524 A1 | 2/2000 |
| WO | 0032137 A1 | 6/2000 |

* cited by examiner

STENT

CROSS-REFERENCE TO RELATED APPLICATIONS

This Application is a continuation of U.S. application Ser. No. 15/401,197, filed Jan. 9, 2017; which is a continuation of U.S. application Ser. No. 13/763,169, filed Feb. 8, 2013, now U.S. Pat. No. 9,554,924; which is a continuation of U.S. application Ser. No. 12/768,447 filed Apr. 27, 2010, now U.S. Pat. No. 8,372,134; which is a continuation of U.S. application Ser. No. 11/059,840 filed Feb. 17, 2005, now U.S. Pat. No. 7,731,742; which is a continuation of U.S. application Ser. No. 10/427,869 filed Apr. 30, 2003.

STATEMENT REGARDING FEDERALLY SPONSORED RESEARCH

Not Applicable.

BACKGROUND OF THE INVENTION

The invention concerns a stent for splinting and/or keeping open a hollow organ, consisting of a tubular body having a diameter which can be changed through axial displacement of the ends of the body relative to each other.

A stent of this type is disclosed in EP 0 901 353 B1.

The known stent not only permits radial widening of vessel narrowings but also splinting or keeping open thereof. The stent is introduced into a hollow organ in its narrowed and lengthened state and radially expanded at the narrowed location of the hollow organ to ensure that the hollow organ assumes its original lumen at this location if possibly permanently.

For automatic expansion, webs are used which are processed into stents. The webs can be lengthened against their unloaded initial structure. If the lengthening or radial deformation is removed, these known stents return into their initial state through radial widening. This effect is used for widening stenoses in hollow organs to prevent their function from being impaired, if possible.

SUMMARY OF THE INVENTION

It is the object of the invention to produce a stent with improved and positionally stable adoption and transmission of the motions of the hollow organs.

This object is achieved in accordance with the invention by the features of claim 1.

The inventive stent therefore has the substantial advantage that it can have sections in the longitudinal direction with returning forces of different strengths. Each stent section may have its own design and/or motion behavior such that stents with reduced total pre-shortening (axial lengthening of the free stent ends with radial compression of a stent) and special migration-suppressing properties can be produced. Due to the fact that the stent sections are connected to each other via elastic tubular sections, the individual stent sections remain highly elastic and can be adjusted to the hollow organ shapes in an improved fashion. The elastic tubular sections (thin highly flexible and tearproof plastic sheets) permit relative motion of the individual stent sections (invagination of a higher or lesser degree which depends on the selected wall thickness and the selected material for the elastic tubular sections). The inventive stent adjusts itself, if necessary, to the peristaltic of hollow organs without migrating. Particular new stent properties can be derived from the distance, separation of the individual stent sections from each other in connection with the elastic tubular sections which interconnect the individual stent sections.

The inventive stent can be expanded by auxiliary means or can be designed as automatically expanding stent.

The inventive stent sections have a woven, braided tubular mesh and/or one or more phase-shifted helices in one or more planes.

This is advantageous in that different support constructions can be used in the individual stent sections in the same stent. The different support constructions or support constructions of different distinction control the motion and deformation behavior of the inventive stent in a defined fashion.

In a further preferred embodiment of the invention, the body is formed in the unloaded expanded state from a first stent section comprising a first diameter, a second and third stent section comprising a second and third diameter and from two elastic tubular sections which connect the first, second and third stent sections.

This is advantageous in that a three-part stent may provided inner lining of a hollow organ which permits e.g. a bordering tumor to protrude elastic tubular sections of an inventive stent into the lumen of the stent. Support and fixing of a stent in the stenosis is further improved thereby (protection from migration).

In a further embodiment of the invention, the diameters of the stent sections vary. This is advantageous in that returning forces of different strengths may form for different locations. The elastic tubular sections easily adjust to cross-sectional changes specifically along a stent and in the unloaded state, a transition from a smaller stent section to a larger stent section and vice versa without projection or creases is possible.

In a further embodiment of the inventive stent, when several helices are provided in several planes, at least one helix has an opposite winding direction. This is advantageous in that the inventive stent obtains reversible torquing (torque) such that during expansion, the pre-torquing is returned and the inventive stent abuts the inner surface of a hollow organ like a screw. This so-called "torquing effect" can be realized in each of the individual stent sections as required.

It is also preferred that the elastic tubular sections are produced from a tissue-compatible plastic material and/or the elastic tubular sections have different diameters in the unloaded state.

This is advantageous in that the inventive stent largely prevents or reduces tissue irritations in the region of its two ends, when placed at its location, and it is possible to coat also the support constructions (webs, helices) with a layer or layers which form elastically tubular sections. Different diameters of the stent sections in the longitudinal direction of a stent are thereby no problem.

In a particularly preferred embodiment of the inventive stent, the body has, viewed in cross-section, a web in the first, second and third stent section and/or one or more helices which are surrounded by one or more elastic plastic layers which merge into the elastic tubular sections in a material-bonding fashion without webs and helices.

This is advantageous in that the inner surface of an inventive stent may have a particularly smooth and/or e.g. hydrophilic layer depending on the requirements and the jacket with plastic layer formed in the outer periphery of the stent fixes the web or helices and the outer and inner plastic coating can merge into the elastic tubular sections along the inventive stent in a material-bonding fashion. This embodiment produces particularly robust stents.

The body of an inventive stent may have a filament in an axial direction in the wall which may serve as a securing thread which ensures that the different stent sections are held together also under increased load and on the other hand this thread may provide X-ray shadow. This is advantageous in that also after a longer prevailing time, the position of the stent in the hollow organ can be examined, determined and proven in an exact fashion. It is clear that also several filaments, e.g. on two opposite sides or in all four cross-sectional quadrants can be worked into the wall of a stent.

The filament worked into the stent in a longitudinal direction may project over the stent as securing thread and serves as pulling thread or for mounting the inventive stent. Several filaments can be worked into the wall of the stent viewed across the periphery of the stent.

In a further embodiment of the invention, the proximal end region of the body of the inventive stent, viewed across the periphery of the body, comprises a worked-in thread whose length projects past the stent. This is advantageous in that such a thread can produce a thread ring similar to a tobacco bag seam which facilitates removal of a placed stent. Pulling together of the proximal stent end like a tobacco bag permits removal of the inventive stent from the bordering hollow organ tissue and pulling out of the hollow organ by the thread.

In a further embodiment, the distal end of the body has a return valve, in particular a foil valve, which is advantageous in that when the inventive stent is placed in the esophagus, liquid or other nutrients can flow only in one direction. The foil valve formed as reflux valve consists of two thin foil sheets which are welded together e.g. at the edges.

Web-free means at the same time no meshes or helices.

Further advantages, of the invention can be extracted from the description of the drawing. The features mentioned above and below can be used in accordance with the invention either individually or in arbitrary combination. The embodiments mentioned are not to be understood as exhaustive enumeration but rather have exemplary character.

The figures show the inventive stent in a highly schematised fashion.

DESCRIPTION OF THE PREFERRED EMBODIMENT

Figure 1:
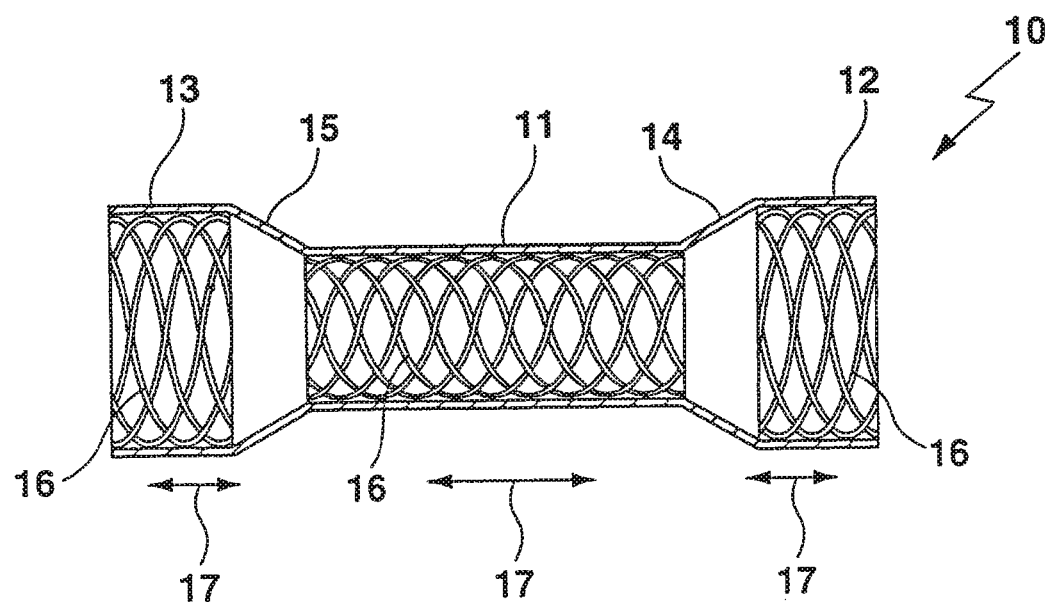
FIG. 1 shows a side view of a first embodiment of an inventive stent.

FIG. 1 shows a stent 10 which is formed from a first stent section 11, a second stent section 12, a third stent section 13, a first elastic tubular section 14 and a second elastic tubular section 15. The stent 10 is shown in an unloaded expanded state. The support construction in the stent sections 11, 12, 13 is a web 16 which may be tubularly braided or woven. The individual filaments of the web may be produced from metal, plastic or carbon. The first stent section 11 may be the tubular web 16 itself or the web 16 is additionally surrounded by a plastic jacket. The gaps (meshes) of the web 16 may be open or closed. The second and third stent section 12, 13 have a larger diameter than the first stent section 11. The web 16 of the first stent section 11 was also chosen as support construction in the stent sections 12, 13. The diameters of the individual filaments of the web 16 in the stent sections 12, 13 may be different from the filament diameters of the filaments used in the first stent section 11.

The stent sections 11, 12, 13 are connected to each other via a first and second elastic tubular section 14, 15. The elastic tubular sections 14, 15 are produced from a flexible thin plastic material, e.g. silicon, and permanently and securely connect the stent sections 11, 12, 13. The elastic tubular sections 14, 15 can safely bridge diameter changes between the individual stent sections 11, 12, 13 and can adjust to the surface contour in a hollow organ without forming gaps. The stent 10 can be lengthened in the direction of arrows 17 and be shortened again after lengthening. The present case concerns an automatically expanding stent 10 which has a smaller diameter in the lengthened state than in the expanded state shown in the figure.

Figure 2:
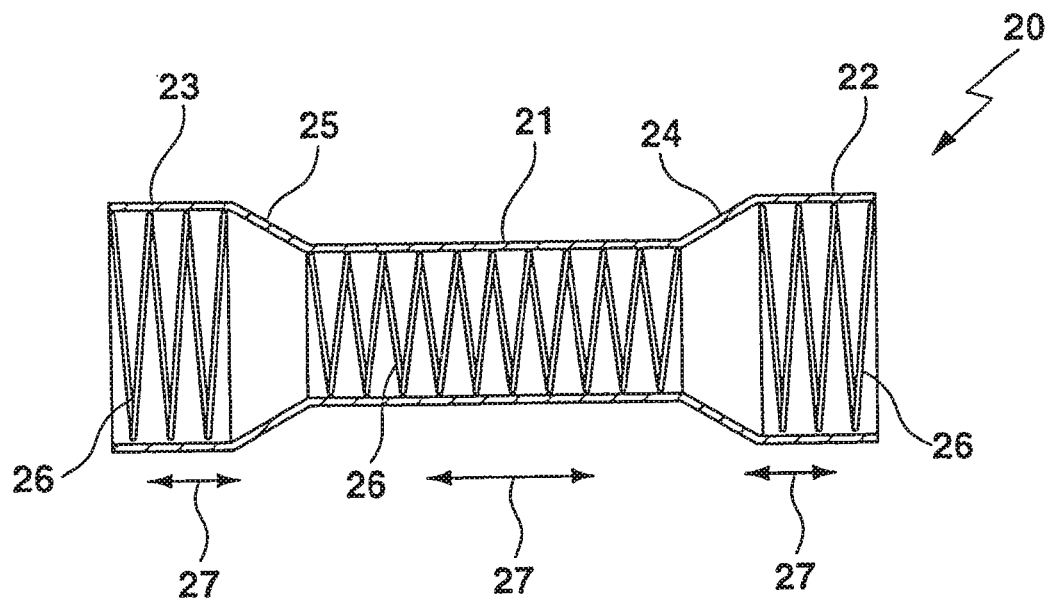
FIG. 2 shows a side view of a second embodiment of an inventive stent.

FIG. 2 shows a stent 20 consisting of a first stent section 21, a second stent section 22, a third stent section 23 and a first and second elastic tubular sections 24, 25. The stent sections 21, 22, 23 are inseparably interconnected via the elastic tubular sections 24, 25. The stent sections 21, 22, 23 have a helix 26 as support construction which is embedded into a stretchable elastic plastic material. The elastic tubular sections 24, 25 have no reinforcing materials such that the stent sections 21, 22, 23 are individually and mutually movable. The stent sections 21, 22, 23 can be lengthened and shortened in the direction of arrows 27. The elastic tubular sections 24, 25 follow the motions of the stent sections 21, 22, 23.

Figure 3:
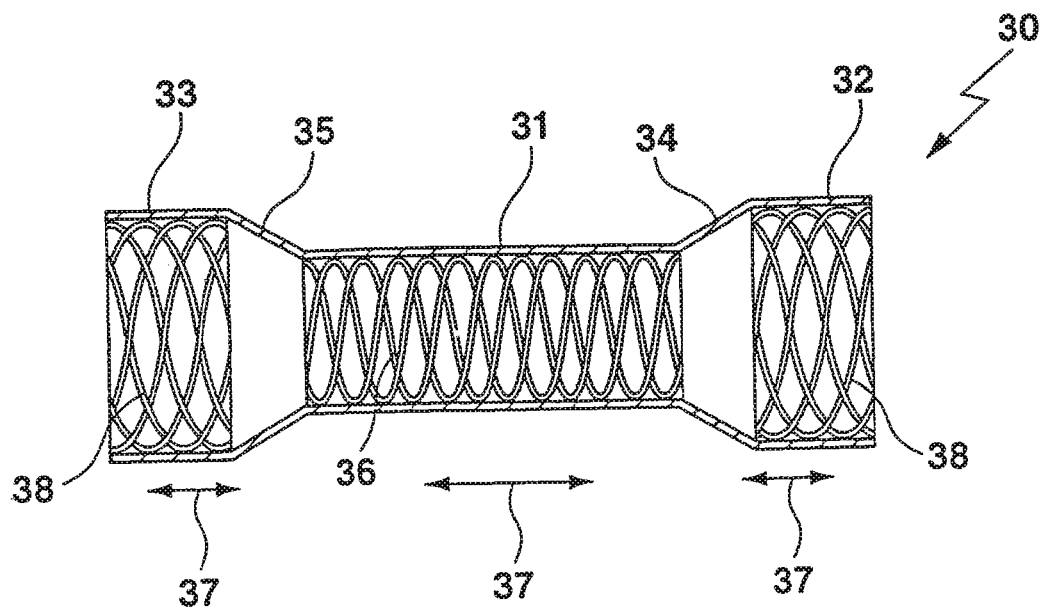
FIG. 3 shows a side view of a third embodiment of an inventive stent.

FIG. 3 shows a stent 30 comprising a first stent section 31, a second stent section 32 and a third stent section 33. The stent sections 31, 32, 33 are permanently connected via a first and a second elastic tubular section 34, 35.

The support construction in the first stent section 31 is a first and second helix 36 of opposite winding directions. A helix 36 is disposed in a first plane in the first stent section 31 embedded in a plastic material, and another helix 36 extends in the second plane which has an opposite winding direction. The support structure of the stent sections 32, 33 is a web 38 which is connected to the first stent section 31 via the elastic tubular sections 34, 35. The stent 30 can be lengthened and shortened in the direction of arrows 37.

Figure 4:
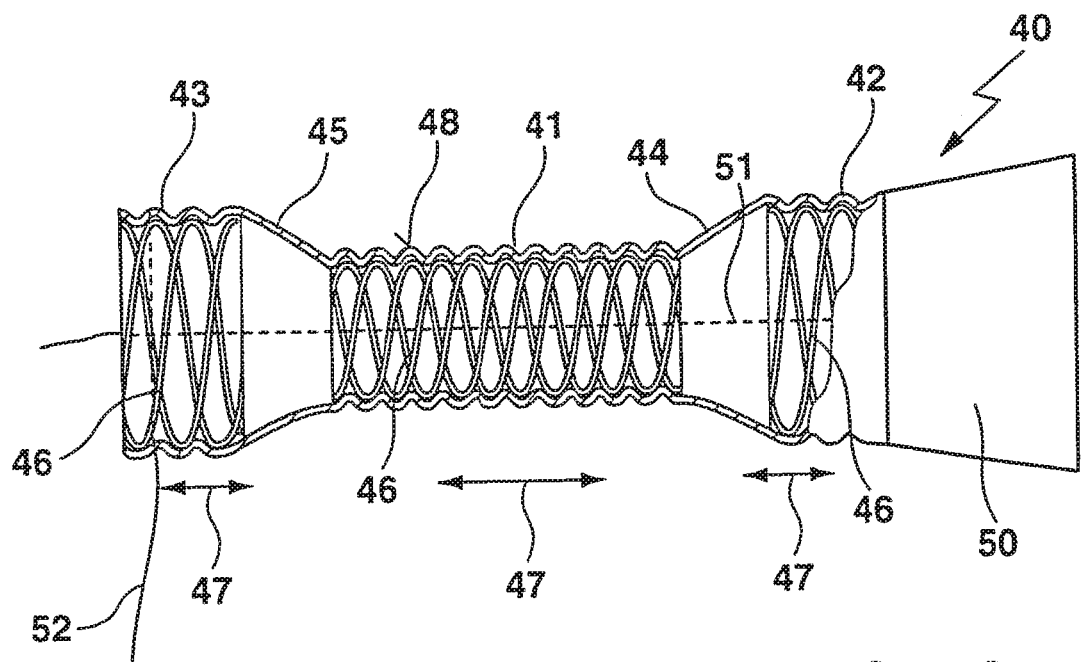
FIG. 4 shows a side view of a fourth embodiment of an inventive stent.

FIG. 4 shows a side view of a further inventive stent 40 which is composed of a first stent section 41, a second stent section 42, a third stent section 43, a first elastic tubular section 44 and a second elastic tubular section 45. The support structure is oppositely winding helices 46 which extend in two different planes. The helices 46 are embedded in a plastic material which is also used for the elastic tubular sections 44, 45. The elastic tubular sections 44, 45 have no helices. The stent 40 can be lengthened in the direction of arrows 47 and subsequently be expanded in a radial direction and shortened in a longitudinal direction. The plastic coating of the helices 46 is selected such that the surface contour 48 is formed on the outer surface which is determined by the selected cross-sectional shape of the helices 46 used. The distal end has a foil valve 50 which permits passage through the stent 40 only from the proximal end towards the distal end. If a fluid or solid flows through the stent 40 from the proximal end to the distal end, the foil valve opens and the foil sheets open i.e. they are moved away from each other. If nothing flows through the stent 40, the foil sheets abut and close the lumen, formed by the stent 40, at one end.

In a longitudinal direction of the stent 40, a filament 51 is worked into the wall of the stent 40 over the entire length which serves as securing thread for the different sections of the stent 40. The filament 51 may project past the stent 40 such that the stent 40 can be mounted or be pulled in the hollow organ via the filament 51. The proximal end of the stent 40 has a thread 52 as thread ring viewed over the periphery of the stent. If the thread 52 is pulled together, the lumen of the third stent section 43 is also highly reduced and the positioned stent 40 is released from the inner surface of the hollow organ. The stent 40 can be removed from a hollow organ via the thread 52.

A stent 10 for transluminal implantation comprises a first, second and third stent section 11, 12, 13 for splinting and/or keeping open a hollow organ, which are connected to each other via elastic tubular sections 14, 15. The stent 10 combines at least three different stent designs in one stent 10 and can be adjusted to the motion behavior of a hollow organ in an improved fashion.

The invention claimed is:

1. A stent comprising:
   a proximal woven or braided tubular stent section having a first diameter, a proximal end, a distal end, and a tubular polymeric cover extending between the proximal end and the distal end of the proximal woven or braided tubular stent section;
   a first tapered polymeric stent section devoid of a woven or braided element and having a proximal end and a distal end,
   wherein the proximal end of the first tapered polymeric stent section has a second diameter equal to the first diameter and the distal end of the first tapered polymeric stent section has a third diameter;
   a central woven or braided tubular stent section having a fourth diameter equal to the third diameter, a proximal end, a distal end, and a tubular polymeric cover extending between the proximal end and the distal end of the central woven or braided tubular stent section;
   a second tapered polymeric stent section devoid of a woven or braided element and having a proximal end and a distal end,
   wherein the proximal end of the second tapered polymeric tubular stent section has a fifth diameter equal to the fourth diameter and the distal end of the second tapered polymeric tubular stent section has a sixth diameter; and
   a distal woven or braided tubular stent section having a seventh diameter equal to the sixth diameter, a proximal end, a distal end, and a tubular polymeric cover extending between the proximal end and the distal end of the distal woven or braided tubular stent section,
   wherein the proximal end of the first tapered polymeric stent section is joined to the distal end of the proximal woven or braided tubular stent section,
   wherein the proximal end of the central woven or braided tubular stent section is joined to the distal end of the first tapered polymeric stent section,
   wherein the proximal end of the second tapered polymeric stent section is joined to the distal end of the central woven or braided tubular stent section, and
   wherein the proximal end of the of the distal woven or braided tubular stent section is coupled to the distal end of the second tapered polymeric stent section.

2. The stent of claim 1, wherein each of the proximal woven or braided tubular stent section, the central woven or braided tubular stent section, and the distal proximal woven or braided tubular stent section is independently moveable relative to one another between a radially collapsed configuration and a radially expanded configuration.

3. The stent of claim 2, wherein the proximal woven or braided tubular stent section has a first length in the radially collapsed configuration and a second length in the radially expanded configuration and the first length is greater than the second length.

4. The stent of claim 2, wherein the central woven or braided tubular stent section has a first length in the radially collapsed configuration and a second length in the radially expanded configuration and the first length is greater than the second length.

5. The stent of claim 2, wherein the distal woven or braided tubular stent section has a first length in the radially collapsed configuration and a second length in the radially expanded configuration and the first length is greater than the second length.

6. The stent of claim 1, wherein each of the proximal woven or braided tubular stent section, the central woven or braided tubular stent section, and the distal proximal woven or braided tubular stent section is independently moveable relative to one another between a longitudinally collapsed configuration and a longitudinally expanded configuration.

7. The stent of claim 1, wherein each of the first tapered polymeric stent section and the second tapered polymeric stent section are independently elastically elongateable.

8. The stent of claim 1, wherein each of the proximal woven or braided tubular stent section, the central woven or braided tubular stent section, and the distal woven or braided tubular stent section are automatically expanding.

9. The stent of claim 1, further comprising a valve attached to the distal end of the distal woven or braided tubular stent section and responsive to fluid flows within the stent.

10. The stent of claim 1, wherein the tubular polymeric cover of the proximal woven or braided tubular stent section, the first tapered polymeric stent section, the tubular polymeric cover of the central woven or braided tubular stent section, the second tapered polymeric stent section, and the tubular polymeric cover of the distal woven or braided tubular stent section form a continuous elastomeric covering for the stent.

11. A stent comprising:
    a proximal woven or braided tubular stent section having a first diameter, a proximal end, a distal end, and a tubular polymeric cover extending between the proximal end and the distal end of the proximal woven or braided tubular stent section;
    a first tapered polymeric stent section devoid of a woven or braided element and having a proximal end and a distal end,
    wherein the proximal end of the first tapered polymeric stent section has a second diameter equal to the first diameter and the distal end of the first tapered polymeric stent section has a third diameter;
    a central woven or braided tubular stent section having a fourth diameter equal to the third diameter, a proximal end, a distal end, and a tubular polymeric cover extending between the proximal end and the distal end of the central woven or braided tubular stent section;
    a second tapered polymeric stent section devoid of a woven or braided element and having a proximal end and a distal end, wherein the proximal end of the second tapered polymeric tubular stent section has a fifth diameter equal to the fourth diameter and the distal end of the second tapered polymeric tubular stent section has a sixth diameter; and a distal woven or braided tubular stent section having a seventh diameter equal to the sixth diameter, a proximal end, a distal end, and a tubular polymeric cover extending between the proximal end and the distal end of the distal woven or braided tubular stent section; and a filament adapted and configured to serve as a securing thread which ensures that the different stent sections are held together;

wherein the proximal end of the first tapered polymeric stent section is joined to the distal end of the proximal woven or braided tubular stent section, wherein the proximal end of the central woven or braided tubular stent section is joined to the distal end of the first tapered polymeric stent section, wherein the proximal end of the second tapered polymeric stent section is joined to the distal end of the central woven or braided tubular stent section, and wherein the proximal end of the of the distal woven or braided tubular stent section is joined to the distal end of the second tapered polymeric stent section.

12. The stent of claim 11, wherein each of the proximal woven or braided tubular stent section, the central woven or braided tubular stent section, and the distal proximal woven or braided tubular stent section is independently moveable relative to one another between a radially collapsed configuration and a radially expanded configuration.

13. The stent of claim 12, wherein the proximal woven or braided tubular stent section has a first length in the radially collapsed configuration and a second length in the radially expanded configuration and the first length is greater than the second length.

14. The stent of claim 12, wherein the central woven or braided tubular stent section has a first length in the radially collapsed configuration and a second length in the radially expanded configuration and the first length is greater than the second length.

15. The stent of claim 12, wherein the distal woven or braided tubular stent section has a first length in the radially collapsed configuration and a second length in the radially expanded configuration and the first length is greater than the second length.

16. The stent of claim 11, wherein each of the proximal woven or braided tubular stent section, the central woven or braided tubular stent section, and the distal proximal woven or braided tubular stent section is independently moveable relative to one another between a longitudinally collapsed configuration and a longitudinally expanded configuration.

17. The stent of claim 11, wherein each of the first tapered polymeric stent section and the second tapered polymeric stent section are independently elastically elongateable.

18. The stent of claim 11, wherein each of the proximal woven or braided tubular stent section, the central woven or braided tubular stent section, and the distal woven or braided tubular stent section are automatically expanding.

19. The stent of claim 11, further comprising a valve attached to the distal end of the distal woven or braided tubular stent section and responsive to fluid flows within the stent.

20. The stent of claim 11, wherein the tubular polymeric cover of the proximal woven or braided tubular stent section, the first tapered polymeric stent section, the tubular polymeric cover of the central woven or braided tubular stent section, the second tapered polymeric stent section, and the tubular polymeric cover of the distal woven or braided tubular stent section form a continuous elastomeric covering for the stent.

* * * * *